US008173181B2

(12) United States Patent
Ferguson et al.

(10) Patent No.: US 8,173,181 B2
(45) Date of Patent: May 8, 2012

(54) METHOD AND COMPOSITION FOR IMPROVED ANABOLISM

(75) Inventors: Chris Ferguson, Boca Raton, FL (US); Sal Abraham, Boca Raton, FL (US)

(73) Assignee: Bio-Engineered Supplements & Nutrition, Inc., Evanston, IL (US)

(*) Notice: Subject to any disclaimer, the term of this patent is extended or adjusted under 35 U.S.C. 154(b) by 0 days.

(21) Appl. No.: 12/942,929

(22) Filed: Nov. 9, 2010

(65) Prior Publication Data

US 2011/0111066 A1 May 12, 2011

Related U.S. Application Data

(60) Provisional application No. 61/259,633, filed on Nov. 9, 2009.

(51) Int. Cl.
*A61K 36/00* (2006.01)
*A61K 36/296* (2006.01)
*A61K 36/704* (2006.01)
*A61K 36/488* (2006.01)
*A61K 36/734* (2006.01)
*A61K 36/254* (2006.01)
*A61K 36/48* (2006.01)
*A61K 36/73* (2006.01)

(52) U.S. Cl. ......... 424/725; 424/728; 424/757; 424/765
(58) Field of Classification Search .................. None
See application file for complete search history.

(56) References Cited

U.S. PATENT DOCUMENTS

| | | | |
|---|---|---|---|
| 3,725,437 | A | 4/1973 | Nagoya et al. |
| 4,100,160 | A | 7/1978 | Walser |
| 4,677,121 | A | 6/1987 | Walser et al. |
| 5,091,560 | A | 2/1992 | Rowland |
| 5,492,713 | A | 2/1996 | Sommermeyer |
| 6,100,287 | A | 8/2000 | Stevens et al. |
| 2004/0185069 | A1* | 9/2004 | Gupta ........................ 424/401 |
| 2004/0204382 | A1* | 10/2004 | Henderson et al. ............. 514/52 |
| 2005/0287204 | A1* | 12/2005 | Hageman et al. ............ 424/451 |
| 2008/0076721 | A1* | 3/2008 | Abraham et al. .............. 514/18 |
| 2008/0108698 | A1 | 5/2008 | Hietala |

OTHER PUBLICATIONS

Mann et al., Expression of Amino Acid Transport Systems in Cultured Human Umbilical Vein Endothellal Cells, Journal of Physiology, 1989, 325-339, vol. 410.
Manna et al., Resveratrol Suppresses TNF-Induced Activation of Nuclear Transcription Factors NF-kB, Activator Protein-1, and Apoptosis: Potential Role of Reactive Oxygen Intermediates and Lipid Peroxidation, The Journal of Immunology, 2000, 6509-6519, vol. 164.
McCarty et al., Up-regulation of PPARc coactivator-1a as a strategy for preventing and reversing insulin resistance and obesity, Medical Hypotheses, 2005, 399-407, vol. 64.
Middelbos et al., Effects of dietary supplementation of DL-methionine or 2-hydroxy-4-(methylthio)-butanoic acid on food intake, nutrient digestibility, nitrogen balance, and urinary and blood metabolites in healthy, growing dogs, Archives of Animal Nutrition, Aug. 2006, 301-306, vol. 60(4).
Park et al., Resveratrol stimulates glucose transport in C2C12 myotubes by activating AMP-activated protein kinase, Experimental and Molecular Medicine, Apr. 2007, 222-229, vol. 39(2).
Perfumi et al., Adaptogenic and Central Nervous System Effects of Single Doses of 3% Rosavin and 1% Salidroside Rhodiola rosea L. Extract in Mice, Phytother. Res., 2007, 37-43, vol. 21.
Qian et al., Regulation of Cbfa1 Expression by Total Flavonois of Herba Epimedii, Endocrine Journal, 2006, 87-94, vol. 53(1).
Rath et al., Effects of Humic Acid on Broiler Chickens, Poultry Science, 2006, 410-414, vol. 85.
Revelli et al., Modulation in vivo of f-adrenergic-receptor subtypes in rat brown adipose tissue by the thermogenic agonist Ro 16/8714, Biochem. J., 1992, 743-746, vol. 286.
Ribeiro et al., Effects of 2-Hydroxy-4-(Methylthio)Butanoic Acid and Dlmethionine on Broiler Performance and Compensatory Growth After Exposure to Two Different Environmental Temperatures, J. Appl. Poult. Res., 2001, 419-426, vol. 10.
Saavedra et al., Demonstration and Distribution of Phenylethanolamine in Brain and Other Tissues, Proc. Nat. Acad. Sci., Mar. 1973, 769-772, vol. 70(3).
Scatena et al., Effects of gemfibrozil on the oxygen transport properties of erythrocytes, Br. J. Clin. Pharmac., 1995, 25-30, vol. 39.
Shevtsov et al., A randomized trial of two different doses of a SHR-5 Rhodiola rosea extract versus placebo and control of capacity for mental work, Phytomedicine., 2003, 95-105, vol. 10.
Tadic et al., Anti-inflammatory, Gastroprotective, Free-Radical-Scavenging, and Antimicrobial Activities of Hawthorn Berries Ethanol Extract, J. Agric. Food Chem., 2008, 7000-7009, vol. 56.
Tolonen et al., Phenylpropanoid Glycosides from Rhodiola rosea, Chem. Pharm. Bull., Apr. 2003, 467-470, vol. 51 (4).
Vazquez-Anon et al., The Use of Methionine Hydroxy Analog in Aquaculture Feeds, Novus International, 2004, 1-8.
Vazquez-Anon et al., Evidence for 2-Hydroxy-4(Methylthio) Butanoic Acid and DL-Methionine Having Different Dose Responses in Growing Broilers, Poultry Science, 2006, 1409-1420, vol. 85.
Verhoeven et al., The metabolism of phytanic acid and pristanic acid in man: A review, J. Inher. Metab. Dis., 1998, 697-728, vol. 21.
Wang et al., Tissue distribution and excretion of resveratrol in rat after oral administration of Polygonum cuspidatum extract (PCE), Phytomedicine, 2008, 859-866, vol. 15.
Watanabe et al., Reduction in Hemoglobin—Oxygen Affinity Results in the Improvement of Exercise Capacity in Mice with Chronic Heart Failure, Journal of the American College of Cardiology, 2008, 779-786, vol. 52(9).

(Continued)

*Primary Examiner* — Qiuwen Mi
(74) *Attorney, Agent, or Firm* — Amin Talati, LLC; Janine A. Moderson; George M. Carrera, Jr.

(57) ABSTRACT

Nutritional compositions are provided containing at least one PPAR agonist, at least one PGC-1alpha agonist, and at least one creatine derivative. Methods of promoting anabolism and improving or enhancing physical performance using the compositions are provided. The compositions and methods can be combined with physical training or exercise.

10 Claims, No Drawings

OTHER PUBLICATIONS

Wolter et al., Piceatannol, a Natural Analog of Resveratrol, Inhibits Progression through the S Phase of the Cell Cycle in Colorectal Cancer Cell Lines, J. Nutr., 2002, 298-302, vol. 132.

Xiao et al., Constituents from Polygonum cuspidatum, Chem. Pharm. Bull., 2002, 605-608, vol. 50(5).

Yasuda et al., Antipyretic, Analgesic and Muscle Relaxant Activities of Pueraria Isoflavonoids and Their Metabolites From Pueraria lobata Ohwi-a Traditional Chinese Drug, Biol. Pharm. Bull., 2005, 1224-1228, vol. 28(7).

Yi et al., Estimation of the true ileal digestible lysine and sulfur amino acid requirement and comparison of the bioefficacy of 2-hydroxy-4-(methylthio)butanoic acid and DL-methionine in eleven- to twenty-six-kilogram nursery pigs, J. Anim. Sci., 2006, 1709-1721, vol. 84.

Zhang et al., The testosterone mimetic properties of icariin, Asian J. Androl., 2006, 601-605, vol. 8(5).

Ali, Z. et al. Phenylalkanoids and monoterpene analogues from the roots of Rhodiola rosea. Feb. 2008;74(2):178-81. (Abstract only).

Bruins, H.W. et al. Growth-promoting activity of L-lyxoflavin. Proc Soc Exp Biol Med. Nov. 1951; 78(2):535-536.

Bu, X. et al. Chemical study of Alpinia officinarum. Zhong Yao Cai. Feb. 2000;23(2):84-87. (English Abstract only).

Cerbon-Ambriz, J. et al. Lactate and pyruvate increase the incorporation of [3H]proline into collagen [3H] hydroxyproline in liver slices of CCI4 cirrhotic rats. Lab Invest. Oct. 1987;57(4):392-396. (Abstract only).

Chang, Q. et al. Simultaneous determination of ten active components in traditional Chinese medicinal products containing both Gegen (Pueraria lobata) and Danshen (Salvia miltiorrhiza) by high-performance liquid chromatography. Phytochem Anal. Jul. 2008;19(4):368-375. (Abstract only).

Chanoine, F. et al. Absorption, distribution, elimination and metabolism of 14C-heptaminol hydrochloride in rat. Arzneimittelforschung. 1981;31(9):1430-1435. (Abstract only).

Chen, K.M. et al. Icariin enhances the osteogenic differentiation of bone marrow stromal cells but has no effects on the differentiation of newborn calvarial osteoblasts of rats. Pharmazie. Oct. 2007;62(10):785-789. (Abstract only).

Chen, Q.G. et al. Effects of Rhodiola rosea on body weight and intake of sucrose and water in depressive rats induced by chronic mild stress. Zhong Xi Yi Jie He Xue Bao. Sep. 2008;6(9):952-955. (Chinese, English Abstract only).

Chen, Y.B. et al. Study on the stability of resveratrol in rhizoma polygoni cuspidati. Zhong Yao Cai.Jul. 2007;30 (7):805-807. (English Abstract only).

Cooperman, J.M. et al. A critique of the biological activity of L-Lyxoflavin. Proc Soc Exp Biol Med. Oct. 1952;81 (1):57-62.

Damron, B.L. et al. 2-Hydroxy-4 (methylthio) butanoic acid as a drinking water supplement for broiler chicks. Poult Sci. Oct. 1992;71(10):1695-1699. (Abstract only).

Darbinyan, V. et al. Rhodiola rosea in stress induced fatigue—a double blind cross-over study of a standardized extract SHR-5 with a repeated low-dose regimen on the mental performance of healthy physicians during night duty. Phytomedicine. Oct. 2000;7(5):365-371.

De Bock, K. et al. Acute Rhodiola rosea intake can improve endurance exercise performance. Int J Sport Nutr Exerc Metab. Jun. 2004;14(3):298-307.

Feng, K. et al. Effect of five species of Epimedium on growth of cartilage and proliferation of cartilage cell in vitro. Zhongguo Zhong Yao Za Zhi. Dec. 2006;31(24):2065-2067. (English Abstract only).

Ferreira, M.J. et al. Effects of piceatannol derivatives in the antiproliferative activity of the anticancer-drug doxorubicine and on apoptosis induction in MDR cancer cell lines. Planta Medica. 2006;72(11):998. (Abstract only).

Fontas, B. et al. Heptaminol hydrochloride as an epithelium transporter. Can J Physiol Pharmacol. Jul. 1990;68 (7):791-799. (English Abstract only).

Friedrich, M. et al. Transport of L-leucine hydroxy analogue and L-lactate in human small intestinal brush border membrane vesicles. Eur J Clin Invest. Feb. 1992;22(2):73-78.

Gardner, T.S. et al. L-Lyxoflavin. Arch Biochem. Nov. 1951;34(1):98-104.

Garlich, J.D. Response of broilers to DL-methionine hydroxy analog free acid, DL-methionine, and L-methionine. Poult Sci. Aug. 1985;64(8):1541-1548. (Abstract only).

Hegedüs, M. et al. Effect of methionine and its derivatives on the weight gain and protein utilisation of growing rats. Acta Vet Hung. 1998;46(4):421-429. (Abstract only).

Khayyal, M.T. et al. Blood pressure lowering effect of an olive leaf extract (Olea europaea) in L-Name induced hypertension in rats. Arzneimittelforschung. 2002;52(11):797-802. (Abstract only).

Kucinskaite, A. et al. Experimental analysis of therapeutic properties of Rhodiola rosea L. and its possible application in medicine. Medicina (Kaunas). 2004;40(7):614-619. (English Abstract only).

Ma, H.P. et al. Effects of rat serum containing total flavonoid extract of Epimedium sagittatum on development of osteoblasts. Zhongguo Zhong Yao Za Zhi. Apr. 2008;33(8):928-931. (English Abstract only).

Martino, E. et al. Influence of the extraction mode on the yield of hyperoside, vitexin and vitexin-2"-O-rhamnoside from Crataegus monogyna Jacq. (hawthorn). Phytochem Anal. Jul. 2008. (Abstract only).

Mège, R.M. et al. Is intercellular communication via gap junctions required for myoblast fusion? Cell Adhes Commun. Aug. 1994;2(4):329-343. (Abstract only).

Nian, H. et al. Prevention of bone loss by aqueous extract of Epimedii sagittatum in an ovariectomized rat model of osteoporosis. Zhong Xi Yi Jie He Xue Bao. Nov. 2006;4(6):628-633.

Parente, J.A. et al. Drugs that suppress hepatic fat synthesis in starved-refed BHE/cdb rats also have an effect on muscle protein synthesis. Proc Soc Exp Biol Med. Nov. 1993;204(2):172-179. (Abstract only).

Pouttias, B. et al. Heptaminol chlorhydrate: new data. Ann Pharm Fr. 1991;49(3):127-138. (English Abstract only).

Richards, J.D. et al. Comparative in vitro and in vivo absorption of 2-Hydroxy-4(methylthio)butanoic acid and methionine in the broiler chicken. Poult Sci. Sep. 2005;84(9):1397-1405.

Shorb, M.S. Growth-promoting activity of L-lyxoflavin for Lactobacillus lactis. Proc Soc Exp Biol Med. Apr. 1952;79 (4):611-614.

Snell, E. et al. Growth-promotion by lyxoflavin. II. Relationship to riboflavin in bacteria and chicks. Proc Soc Exp Biol Med. Apr. 1953;82(4):583-590.

Sokolova, V.E. et al. Anabolic action flavonoids. Farmakol Toksikol. May-Jun. 1978;41(3):323-327. (English Abstract only).

Spasov, A.A. et al. A double-blind, placebo-controlled pilot study of the stimulating and adaptogenic effect of Rhodiola rosea SHR-5 extract on the fatigue of students caused by stress during an examination period with a repeated low-dose regimen. Phytomedicine. Apr. 2000;7(2):85-89.

Talbert, R. Shilijit Moomiyo. Monograph. Materia Medica. Aug. 2004;1-16.

Tang, X.H. Activation of retinoid x receptors by phytanic acid and docohexaenoic acid: role in prevention and therapy of prostate cancer. Annual Summary. Weill Medical College of Cornell University. Jan. 2005. U.S. Army Medical Research and Material Command.

Wahlstrom, R.C. et al. Effect on lyxoflavin on growth of baby pigs fed a synthetic diet. Proc Soc Exp Biol Med. Apr. 1952;79(4):636-639.

Xiao, Q. et al. Effects of Icariin on expression of OPN mRNA and type I collagen in rat osteoblasts in vitro. J Huazhong Univ Sci Technolog Med Sci. 2005;25(6):690-692. (Abstract only).

Yong, E.L. et al. Standardization and evaluation of botanical mixtures: lessons from a traditional Chinese herb, Epimedium, with oestrogenic properties. Novartis Found Symp.2007;282:173-188. (Abstract only).

Yu, Z. et al. Effects of Puerariae isoflavone on blood viscosity, thrombosis and platelet function. Zhong Yao Cai. Sep. 1997;20(9):469-469. (English Abstract only).

Zheng, G. et al. Estrogen-like effects of puerarin and total isoflavones from Pueraria lobata. Zhong Yao Cai. Aug. 2002;25(8):566-568. (English Abstract only).

Zheng, G. et al. Hypocholesterolemic effect of total isoflavones from Pueraria lobata in ovariectomized rats. Zhong Yao Cai. Apr. 2002;25(4):273-275. (English Abstract only).

Abidov et al., Effect of Extracts from Rhodiola Rosea and Rhodiola Crenulata (Crassulaceae) Roots on ATP Content in Mitochondria of Skeletal Muscles, Bulletin of Experimental Biology and Medicine, Dec. 2003, 664-666, vol. 136(6).

Abidov et al., Extract of Rhodiola Rosea Radix Reduces the Level of C-Reactive Protein and Creatinine Kinase in the Blood, Bulletin of Experimental Biology and Medicine, Jul. 2004, 73-75, vol. 138(7).

Akhmedzhanova et al., Alkaloids and Flavonoids of Oxytropis Muricata, Chemistry of Natural Compounds, 1997, 326-328, vol. 33(3).

Allard et al., Action of heptaminol hydrochloride on contractile properties in frog isolated twitch muscle fibre, Br. J. Pharmacol., 1991, 714-718, 104.

Rhodiola rosea (Monograph), Alternative Medicine Review, Oct. 2002, vol. 421(3).

Aria et al, Changes in Activities of Enzymes Related to Malate-Aspartate Shuttle in Leukocytes from Dogs Gives a Herb Supplement, J. Vet. Med. Sci., 2001, 695-697, vol. 63(6).

Aria et al., Effect of herb supplement on hepatic enzyme activities in ddY mice, Laboratory Animals, 2001, 288-291, vol. 35.

Assimacopoulos-Jeannet et al., Effect of a beta-adrenergic agonist on glucose transport and insulin-responsive glucose transporters (GLUT4) in brown adipose tissue of control and obese fa/fa rats, Pfliigers Arch, 1992, 52-58, vol. 421.

Battistelli et al., Rhodiola Rosea as antioxidant in red blood cells: ultrastructural and hemolytic behavior, European Journal of Histochemistry, Jul.-Sep. 2005, 243-254, vol. 49(3).

Bauerdick et al., Therapy with essential amino acids and their nitrogen-free analogues in severe renal failure, The American Journal of Clinical Nutrition, 1793-1796, Oct. 1978, vol. 31.

Benlhabib et al., Composition, Red Blood Cell Uptake, and Serum Protein Binding of Phytoestrogens Extracted from Commercial Kudzu-Root and Soy Preparations, Journal of Medicinal Food, 2002, 109-124, vol. 5(3).

Berthiau et at., Decrease in internal H + and positive inotropic effect of heptaminol hydrochloride: a 31p n.m.r. spectroscopy study in rat isolated heart, Br. J. Pharmacol., 1989, 1233-1240, vol. 98.

Boebel et al., Comparative Utilization of the a-Keto and D- and L-a-Hydroxy Analogs of Leucine, Isoleucine and Valine by Chicks and Rats1'2, J. Nutr, 1982, 1929-1939, vol. 112.

Bondarenko et al., Determination of the Position of the Acyl Groups and the Nature of Some Amino Alcohols in Native Ester Alkaloids of the Genus Veratrum, Khimiya Prirodnykh Soedinenii, 1970, 440-443, vol. 6(4).

Bucci, Selected herbals and human exercise performance, Am. J. Clin. Nutr. 2000, 624S-636S, vol. 72(suppl).

Burgos et al., Studies in vitro on shuttle systems of mouse spermatozoa, Biochem. J., 1982, 419-417, vol. 202.

Chawla et al., Utilization of a-Keto and a-Hydroxy Analogues of Valine by the Growing Rat, Aug. 1974, The Journal of Clinical Investigation, 271-277, vol. 54.

Connick et al., Identification of Volatile Allelochemicals from Amaranthus Palmeri S. Wats, Journal of Chemical Ecology, 1987, 463-472, vol. 13(3).

Coquet et al., Identification of new molecules extracted from Quercus suber L. cork, C. R. Biologies, 2008, 853-858, vol. 331.

Coronel et al., Properties of the branched-chain 2-hydroxy acid/2-oxo acid shuttle in mouse spermatozoa, Biochem. J., 1986, 853-858, vol. 235.

Cusack, Blackwell Publishing Asia Effects of a dietary complex of humic and fulvic acids (FeedMAX 15™) on the health and production of feedlot cattle destined for the Australian domestic market, Australian Veterinary Journal, Jan.-Feb. 2008, 46-49, vol. 86(1-2).

Dailey et al, Nonpolar Lipids of Amaranthus palmeri S. Wats. 2. Unsaturated Esters and Free Fatty Acids, Sterols, and Triterpenols, J. Agric. Food Chem., 1997, 3914-3920, vol. 45.

De Sanctis et al., in vitro protective effect of Rhodiola rosea extract against hypochlorous acid-induced oxidative damage in human erythrocytes, BioFactors, 2004, 147-159, vol. 20.

Erdemoglu et al., Bioassay-guided isolation of anti-inflammatory and antinociceptive principles from a folk remedy, Rhododendron ponticum L. leaves, Journal of Ethnopharmacology, 2008, 172-178, vol. 119.

Feng et al., Efficacy of methionine hydroxyl analog and DL methionine as methionine source for growing pigs, Journal of Animal and Veterinary Advances, 2006, 135-142, vol. 5(2).

Fernzandez-Navarro et al., Maslinic acid added to the diet increases growth and protein-turnover rates in the white muscle of rainbow trout (Oncorhynchus mykiss), Comparative Biochemistry and Physiology, Part C, 2008, 158-167, vol. 147.

Fernzandez-Navarro et al., Maslinic acid as a feed additive to stimulate growth and hepatic protein-turnover rates in rainbow trout (Onchorhynchus mykiss), Comparative Biochemistry and Physiology, Part C, 2006, 130-140, vol. 144.

Fong et al., Hawthorn, J. Cardiovasc. Nurs., 2002, 1-8, vol. 16(4).

Gloerich et al., Metabolism of phytol to phytanic acid in the mouse, and the role of PPARa in its regulation, J. Lipid Res., 2007, 77-85, vol. 48.

Gonzales-Esquerra et al., Evidence of a Different Dose Response in Turkeys When Fed 2-Hydroxy-4 (Methylthio) Butanoic Acid Versus DL-Methionine, Poultry Science, 2007, 517-524, vol. 86.

Gordon, Mumie, Gordon Research Institute, http://gordonresearch.com/Product_Research/Beyond_GHS/mumie.html, 2006.

Heim et al., Phytanic acid, a natural peroxisome proliferatoractivated receptor (PPAR) agonist, regulates glucose metabolism in rat primary hepatocytes, FASEB J., May 2002, 718-720, vol. 16.

Hoffer et al., a-Keto and a-Hydroxy Branched-Chain Acid Interrelationships in Normal Humans, J. Nutr., 1993, 1513-1521, vol. 123.

Jang et al., Puerariafuran, a New Inhibitor of Advanced Glycation End Products (AGEs) Isolated from the Roots of Pueraria lobata, Chem. Pharm. Bull., 2006, 1315-1317, vol. 54(9).

Jeon et al., Antitumor activity of spinasterol isolated from Pueraria roots, Experimental and Molecular Medicine, Apr. 2005, 111-120 vol. 37(2).

Ji et al., Effects of dietary humic substances on pig growth performance, carcass characteristics, and ammonia emission, J. Anim. Sci., 2006, 2482-2490, vol. 84.

Kaule et al., Prolyl Hydroxylase Activity in Tissue Homogenates of Annelids from Deep Sea Hydrothermal Vents, Matrix Biolog, 1998, 205-212, vol. 17.

Kelly, Rhodiola rosea: A Possible Plant Adaptogen.(evaluation of therapeutic properties), Alternative Medicine Review, Jun. 2001, 293-302, vol. 6(3).

Kim et al., Antioxidative effects of Cinnamomi cassia and Rhodiola rosea extracts in liver of diabetic mice, BioFactors, 2006, 209-219, vol. 26.

Kimura et al., Resveratrol Isolated from Polygonum cuspidatum Root Prevents Tumor Growth and Metastasis to Lung and Tumor-Induced Neovascularization in Lewis Lung Carcinoma-Bearing Mice, J. Nutr., 2001, 1844-1849, vol. 131.

Knight et al., Comparative Absorption of 2-Hydroxy-4-(Methylthio)-butanoic Acid and L-Methionine in the Broiler Chick, J. Nutr., 1984, 2179-2186, vol. 114.

Koivunen et al., Inhibition of Hypoxia-inducible Factor (HIF) Hydroxylases by Citric Acid Cycle Intermediates, The Journal of Biological Chemistry, Feb. 16, 2007, 4524-4532, vol. 282(7).

Lagouge et al., Resveratrol Improves Mitochondrial Function and Protects against Metabolic Disease by Activating SIRT1 and PGC-1a, Cell, Dec. 2006, 1109-1122, vol. 127.

Lau et al., A Glycoside Flavonoid in Kudzu, Applied Biochemistry and Biotechnology, 2005, 783-794, vol. 121-124.

Lin et al., Metabolic control through the PGC-1 family of transcription coactivators, Cell Metabolism, Jun. 2005, 361-370, vol. 1.

Ding et al., Icariin promotes expression of PGC-1α, PPARα, and NRF-1 during cardiomyocyte differentiation of murine embryonic stem cells in vitro, Acta. Pharmacol. Sin., Oct. 2007, 1541-1549, vol. 28(10).

Liu et al., Effects of trans-Resveratrol from Polygonum cuspidatum on Bone Loss Using the Ovariectomized Rat Model, J. Med. Food., 2005, 14-19, vol. 8(1).

Liu et al., Impact of feeding 2-hydroxy-4-(methylthio)butanoic acid and DL-methionine supplemented maize—soybean—rapeseed meal diets on growth performance and carcase quality of broilers, British Poultry Science, Apr. 2007, 190-197, vol. 48(2).

Liu et al., Maslinic Acid Reduces Blood Glucose in KK-Ay Mice, Biol. Pharm. Bull., 2007, 2075-2078, vol. 30(11).

Ma et al., Rhodiolosides A-E, Monoterpene Glycosides from Rhodiola rosea, Chem. Pharm. Bull., 2006, 1229-1233, vol. 54(8).

* cited by examiner

METHOD AND COMPOSITION FOR IMPROVED ANABOLISM

This application claims the benefit of earlier filed U.S. Provisional Patent Application Ser. No. 61/259,633 filed on Nov. 9, 2009.

FIELD OF THE INVENTION

A composition that, through the stimulation of peroxisome proliferator-activated receptors (PPARs) and peroxisome proliferator-activated receptor-γ coactivator (PGC-1α) during training, regulates athletic function and stimulates the anabolic pathway is provided. The composition may be utilized as a dietary supplement or conventional food to improve athletic function and/or muscle growth and development via improved anabolism.

BACKGROUND

Anabolism is a key factor in the process of muscle growth for athletes and body builders. Anabolism is comprised of multiple metabolic pathways, constructing larger molecules from their building blocks. Energy is a necessary part of these metabolic pathways. In contrast, catabolism is the deconstruction of large molecules into smaller ones. Anabolism is fueled by both the small molecules of catabolism as well as an energy source, such as, but not limited to, adenosine triphosphate (ATP). The anabolic process and related anabolic hormones stimulate protein synthesis and muscle growth.

Anabolic reactions are synthesis reactions and are endergonic, meaning that they consume more energy than they produce. Anabolism is the process of chemical reactions that combine simple molecules and monomers to form the body's complex structural and functional components. Glucose may take part in or be formed via several anabolic reactions such as, for example, synthesis of glycogen or the synthesis of new glucose molecules from byproducts of protein and lipid breakdown, i.e., gluconeogenesis.

One way of promoting anabolism is through the use of a dietary supplement or drug. However, many anabolic stimulation compositions are illegal or have been banned from use by athletes in a number of professional, collegiate, and amateur sports. Additionally, anabolic stimulating products also generally tend to have undesired side effects that can be harmful to the health of an individual. Thus, there is a need and a demand for a dietary ingredient or composition which can promote anabolism without undesirable side effects and/or which is suitable for use by athletes.

For the most part, anabolism is increased where there is an energy source and a way to synthesize proteins and therefore build new muscle. One energy source is ATP. Alternative energy sources include compounds or methods to increase metabolism. The ability and rate at which the body can spare and replenish energy is critical for anabolism.

Peroxisome proliferator-activated receptors (PPARs) are nuclear receptor protein transcription factors that operate to regulate the expression of genes. PPARs have been identified in a wide variety of human tissue and play an essential role in the regulation of processes such as cellular differentiation, development, and metabolism. The oral use of ingredients which increase the activity of PPARs is one approach to fostering anabolism and regulating athletic function.

Peroxisome proliferator-activated receptor-γ coactivator (PGC)-1α ("PGC-1alpha") regulates energy metabolism and promotes mitochondrial biogenesis. Mitochondria convert nutrients into energy. While exercise alone is enough to increase the expression of PGC-1alpha, exercise plus known activators of PGC-1alpha may work together to regulate energy metabolism and promote mitochondrial biogenesis, thereby stimulating anabolism. The oral use of ingredients which affect the synthesis or activity of PGC-1alpha in dietary supplements is another approach to fostering anabolism and regulating athletic function.

A transcription coactivator is defined as a protein or protein complex that increases the probability of a gene being transcribed by interacting with transcription factors but does not itself bind to DNA in a sequence-specific manner. The PPARs are members of a relatively large family of nuclear receptors, all of which are subject to transcriptional coactivation by PCG-1 alpha (Liang, et al., Advan. Physiol. Edu. (2006) 30:145-151).

In view of the above, there is a need and a desire for a dietary supplement including or containing ingredients that help regulate PGC-1alpha and PPARs to foster anabolism and regulate athletic function.

SUMMARY OF THE INVENTION

The presently claimed invention relates to a method for the stimulation of anabolism and, more particularly, the administration to an individual of an effective amount of at least one compound that has an effect on PPAR and at least one compound which has an effect on PGC-1 alpha to enhance or increase anabolic processes in a human subject.

The object of the invention can be obtained, at least in part, by administering to an individual (i.e., a human) a nutritional composition including or containing ingredients that help regulate PGC-1alpha and PPARs to promote greater anabolism. The PGC-1alpha and PPAR regulating sources can be administered alone or in conjunction with compounds that promote muscle formation, promote protein synthesis, stimulate the metabolism or help regulate other hormones that are essential to anabolism.

In accordance with one embodiment, the nutritional composition comprises at least one PPAR agonist and at least one PGC-1alpha agonist.

In accordance with another embodiment, the nutritional composition consists essentially of at least one PPAR agonist and at least one PGC-1alpha agonist.

In a further embodiment, the nutritional composition consists of at least one PPAR agonist and at least one PGC-1alpha agonist.

In a still further embodiment, the nutritional composition can comprise, consist essentially of, or consist of at least one compound that has an effect on PPAR, PGC-1alpha, or both and at least one creatine derivative or creatine containing compound.

In accordance with certain other embodiments, the nutritional composition can further include central nervous system stimulants and/or an energy source to promote protein synthesis and/or increase metabolism.

In accordance with other embodiments, a method for providing a beneficial physical effect can comprise administering to an individual (i.e., a human subject) a therapeutically effective amount of a nutritional composition which comprises, consists essentially of or consists of at least one PPAR agonist and at least one PGC-1alpha agonist. The beneficial physical effect can be improved, enhanced or increased muscle growth, anabolism, anti-catabolism, strength, recovery, endurance, and/or mental focus, mood elevation, improved insulin resistance, increased nitric oxide production, and/or improved energy metabolism.

In accordance with further embodiments, a method for enhancing physical performance can comprise administering to an individual a therapeutically effective amount of a nutritional composition which comprises, consists essentially of or consists of at least one PPAR agonist and at least one PGC-1alpha agonist. Enhanced physical performance includes, for example, improved or enhanced anabolism, anti-catabolism, anti-fatigue, strength, endurance, mental focus, and/or recovery when combined with exercise.

The methods disclosed herein contemplate the administration of a nutritional composition which can provide an improvement in anabolism in comparison to other pre-training, during-training, or post-training compositions. Suitably, the nutritional compound promotes anabolism without unwanted and potentially dangerous side effects generally associated with other products, such as anabolic steroids, that promote anabolism.

As used herein it is understood that the term "creatine containing" may also include derivatives and analogues of creatine and salts or esters thereof.

As used herein it is understood that the term "PGC-1" may include PGC-1α, PGC-1β, PGC-1δ and PGC-1γ. Also contemplated herein for use in the nutritional compositions are PGC-1 agonists, antagonists, and derivatives, conjugates, and salts thereof.

As used herein it is understood that the term "PPAR" may include all peroxisome proliferator-activated receptors, and isoforms thereof. Also contemplated herein for use in the nutritional compositions are PPAR agonists, antagonists, and derivatives, conjugates, and salts thereof.

DETAILED DESCRIPTION

Anabolism is comprised of multiple metabolic pathways, constructing larger molecules from their building blocks. Energy is a necessary part of these metabolic pathways. In contrast, catabolism is the deconstruction of large molecules into smaller ones. Anabolism is fueled by both the small molecules of catabolism as well as an energy source, such as, but not limited to, adenosine triphosphate (ATP). The anabolic process and related anabolic hormones stimulate protein synthesis and muscle growth.

The object of the presently claimed invention can be obtained, at least in part, by administering to an individual (i.e., a human subject) an effective amount of a nutritional composition including one or more ingredients that help regulate PGC-1alpha and/or PPARs. The PGC-1alpha and PPAR regulating sources can be administered alone or in conjunction with compounds that promote muscle formation, promote protein synthesis, stimulate the metabolism, or regulate other hormones that are essential to anabolism.

In accordance with one embodiment, a method for promoting anabolism includes administering to an individual an effective amount of a nutritional composition including PGC-1alpha and PPAR regulators. The PGC-1alpha and PPAR regulating compounds act to induce activity of the PGC-1alpha and PPARs and are agonists.

PPARs are lipid-activated transcription factors that belong to the steroid/thyroid/retinoic acid receptor superfamily. All of their characterized target genes encode proteins that participate in lipid homeostasis. Certain PPARs induce the expression of many genes involved in lipid anabolism. PPARs stimulate anabolic processes such as adipogenesis, lipogenesis and glucose uptake. PPARs also act as nutritional sensors that regulate a variety of homeostatic functions including metabolism, inflammation and development. PPAR-gamma (PPAR-γ) regulates anabolism or storage. The equilibrium between anabolic and catabolic processes is under the control of chondrocytes, which are under the influence of PPARs. PPARs act by dimerizing with receptors that then bind to specific regulatory regions on the DNA of target genes, called peroxisome proliferator response elements (PPREs). When the PPARs (and associated proteins in the PPRE complex) bind to the genes, transcription of the target genes is then increased or decreased, depending on the gene. PPARs bind specific ligands and regulate gene transcription by binding to DNA, and can be activated by various compounds.

PGC-1alpha is a transcriptional coactivator of the PPARs that is thought to control adaptive responses to physiological stimuli. PGC-1alpha has been shown to be upregulated with even a single bout of exercise. This increase may play a role in mediating response to exercise, including cardiovascular and metabolic responses. PGC-1alpha has been linked to adaptive thermogenesis, e.g., response to cold, and participates in carbohydrate and lipid metabolism. Fasting has been shown to increase the activity of PGC-1alpha, while insulin has a suppressive effect on PGC-1alpha. PGC-1alpha has also been shown to prevent muscle damage by certain chemical agents.

In accordance with certain embodiments the PPARs and/or the PGC-1alpha compounds or ingredients can be derived or obtained from a natural source such as, for example, a botanical or herbal source. Examples of natural sources of PPARs and/or PGC-1alpha activator compounds, components or ingredients include, but are not limited to, *Epimedium sagittatum* which is believed to promote PGC-1alpha, PPAR alpha (PPAR-α), and nuclear respiratory factor-1 (NRF-1) expression (i.e., act as an agonist), *Epimedium grandiflorum* which is believed to promote the expression of PGC-1alpha, PPAR-alpha and NRF-1, and Japanese Knotweed which is believed to be a PGC-1alpha agonist. It is noted that the term "PPAR agonist" as used herein comprises naturally occurring botanical sources that include PPAR activator compounds or components.

In accordance with certain other embodiments, the PPARs and/or the PGC-1alpha compounds or ingredients can be in the form of one or more isolated, purified, or naturally-derived compounds such as, for example, resveratrol which is believed to be a PPAR agonist, piceatannol which is believed to be a PGC-1alpha agonist, sodium pyruvate which is believed to be a PGC-1alpha agonist, and phytanic acid which is believe to be a PPAR-α, PPAR-β, and PPAR-γ agonist.

In accordance with certain embodiments, trans-resveratrol, resveratrol derivatives, and resveratrol-related compounds can be included in the nutritional composition as PPAR agonists and to promote or enhance recovery after exercise. Resveratrol has been shown to have many health benefits, including as an anti-inflammatory, blood-sugar regulatory and many cardiovascular benefits.

Piceatannol is the phenolic stilbenoid metabolite of trans-resveratrol which can be found in the seeds of the plant *Euphorbia lagascae* L. Piceatannol is also known as a natural analog of resveratrol and is believed to be a resveratrol precursor. Piceatannol is further believed to contribute to health benefits such as increased aerobic capacity, improved metabolic homeostasis, and/or improved insulin resistance. Piceatannol may work synergistically with creatine phytanate, phytanic acid, Japanese Knotweed, *Rhodiola rosea, Epimedium grandiflorum, Epimedium sagittatum*, and/or sodium pyruvate.

Japanese Knotweed (*Polygonun cuspidatum*) is an herbaceous plant that is a commercial source of resveratrol and is believed to be a PGC-1alpha agonist, an anti-inflammatory agent and acts as a selective estrogen receptor modulator (SERM).

Phytanic acid is a branched-chain fatty acid that is derived from the phytanol side chain of chlorophyll. Phytanic acid is oxidized into pristanic acid. Phytanic acid is believed to be a PPAR-α, β and γ agonist and is also believed to increase nitric oxide production.

In accordance with certain embodiments, the nutritional composition includes one or more PGC-1alpha and PPAR regulating compounds or ingredients in combination with a source of creatine. Suitably, the creatine sources may include salts, esters, derivatives, or conjugates of creatine that further help induce activity of PGC-1alpha and PPARs, such as, for example, creatine heptyl ester, creatine ethyl ester, and the like. Sources of creatine may include creatine salts that act synergistically with other compounds in the invention. Heptanol, heptaminol and heptaminol precursors are contemplated which are anabolic and central nervous system stimulants, and may help increase muscle mass. Another potential creatine source is creatine phytanate, which is believed to improve or enhance strength, endurance and/or muscle size. Other creatine containing salts, solvates, prodrugs, and conjugates are contemplated as useful in the nutritional compositions. Useful creatine containing components include, but are not limited to, creatine monohydrate, Creatine Alpha Amino-N-butyrate, Creatine Ethyl Ester-Beta-Alanine intermixture, Creatinol-O-Phosphate-Malic Acid Interfusion complex, Sodium Creatine Phosphate Matrix, N-phosphatidyl Creatine Heptanoate Ester, Creatine Heptanoate HCl, Ethyl 2-[N-(1-(hexadecanamido)aminomethyl)-N-methylamino]acetate (reduced Creatine Palmitoyl Ethyl Ester HCl), and the like.

In accordance with further embodiments, the nutritional composition can also include an energy source. One suitable energy source is sodium pyruvate which is involved in the cycle that converts glucose to energy (i.e., the Krebs cycle). Enzymes of the Krebs cycle and electron transport chain are located in the mitochondria and it is believed that mitochondrial number and/or improved mitochondrial function may be central to maintaining muscle integrity. Sodium pyruvate has been found to increase the availability of ATP, improve work capacity, and act as a PGC-1alpha agonist. Sodium pyruvate has also been used to promote weight loss.

Another suitable energy source may be in the form of a powder, extract or preparation of *Echeveria glauca*, a succulent plant from the Crassulaceae family. *Echeveria glauca* is believed to increase energy metabolism and may also increase glycolytic enzyme production which support anabolism. Another suitable energy source may be *Panax gingseng* and/or an extract thereof which contains or is enriched in ginsenocides or ginsenosides, a class of steroid glycosides, and triterpene saponins, found exclusively in the plant genus Panax (ginseng).

The nutritional composition can further include one or more anabolic stimulants and/or central nervous system stimulants to help regulate the activity of PPARs to promote anabolism and to act synergistically with other compounds. Examples of suitable anabolic and/or central nervous system stimulants include, but are not limited to hepatanol, heptaminol, L-lyxoflavin, *Oxytropis muricata*, hydroxyphenethylamine, N-benzoyl-2-hydroxyphenethylamine, and N-nicotinoyl-2-hydroxyphenethylamine.

Heptanol is a saturated primary aliphatic alcohol, also known as heptyl alcohol. Heptanol is a heptaminol precursor, an anabolic and a central nervous system stimulant, and can be found naturally in the careless weed (*Amaranthus palmeri*) plant. Heptaminol is an amino alcohol that is also classified as a vasodilator. Heptanol may work in synergy with creatine heptyl ester or creatine ethyl ester to further promote the anabolic pathway.

L-lyxoflavin is a synthetic vitamin, which is similar to riboflavin (vitamin B2) except that the d-ribitol is replaced with d-lyxitol. L-lyxoflavin is a steroisomer of riboflavin that is derived from Lyxol. L-lyxoflavin promotes muscle accretion, increases the efficiency of feed utilization, increases growth rate, and is an anabolic vitamin analog.

*Oxytropis muricata*, hydroxyphenethalamine, N-benzoyl-2-hydroxyphenethylamine and N-nicotinoyl-2-hydroxyphenethylamine are beta-adrenoceptor agonists, anabolic and central nervous system stimulants which are believed to help increase or stimulate muscle growth.

Certain other beneficial compounds and/or natural botanicals, herbs or ingredients may be added to the invention to act synergistically with key ingredients to promote anabolism through the regulation of PPARs, such as PGC-1alpha, or to increase NO production, or for their health benefits. Such beneficial compounds and/or natural ingredients can include, but are not limited to: *Rhodiola rosea*, rosavin and/or salidroside; *Epimedium grandiflorum; Epimedium sagittatum* and/or icariin; compounds and/or ingredients which promote protein synthesis and/or increased growth rate such as alpha-hydroxy-isovaleric acid, alpha-hydroxy-isocaproic acid, alpha-hydroxy-beta-valeric acid, Lespedine (kamferol-3,7-dirhamnoside), and/or Shilajit moomiyo extract with fulvic acid and/or humic acid; compounds and/or ingredients which are or contain antioxidants and/or promote improve muscle mass such as kudzu powders, extracts or preparations, robinin, hyperin, and/or hawthorn powders, extracts or preparations; and compounds and/or ingredients which promote insulin sensitivity such as loquat leaf extract and/or maslinic acid.

*Rhodiola rosea*, a plant in the Crassulaceae family, is an adaptogen and is a natural herb that is known to increase a body's resistance to stress, trauma, anxiety and fatigue. The glycoside compounds Rosavin(s) and salidroside(s) are believed to be responsible for the antidepressant and anxiolytic actions of this plant. *Rhodiola rosea* is also thought to improve exercise capacity, activate the synthesis of adenosine triphosphate (ATP), act as an anti-inflammatory agent, reduce fatigue and is a PGC-1alpha agonist. *Rhodiola rosea* is generally used to reduce recovery time after intense workouts. In accordance with certain embodiments, *Rhodiola rosea* such as in the form of an extract standardized for rosavins and/or salidorsides can be included in the nutritional composition as PPAR/PCG-1alpha agonists and/or as an energy source. In accordance with certain other embodiments, rosavin, salidroside, and/or an alternative botanical source of rosavin and/or salidroside can be included in the nutritional composition.

*Epimedium grandiflorum* is an herbaceous flowering plant in the family Berberidaceae. The active ingredient in *Epimedium grandiflorum* is icariin, which is known to increase nitric oxide. *Epimedium grandiflorum* is also believed to promote the expression of PGC-1alpha, PPAR-alpha and NRF-1.

Alpha-hydroxy-isovaleric acid, alpha-hydroxy-isocaproic acid and alpha-hydroxy-beta-methyl valeric acid are hydroxy acids. All three hydroxy acids have growth promoting capacity, increase protein synthesis and improve recovery time from exercise. Alpha-hydroxy amino acids may also have a standalone anabolic effect. Additional useful hydroxy acids include alpha-hydroxy-gamma-methylthiobutyric acid, alpha-hydroxy-beta-phenylpropionic acid, alpha-hydroxy-beta-imidazolepropionic acid, alpha-hydroxy-beta-hydroxybutyric acid, alpha-hydroxy-gamma-aminocaproic acid, alpha-hydroxy-gamma-guanidinovaleric acid, and the like.

*Epimedium sagittatum* is an herbal treatment used to increase stamina. *Epimedium sagittatum* promotes PGC-1alpha, PPAR-alpha, and NRF-1 expression, has antiosteoporotic effects and increases testosterone levels. In accordance with certain embodiments, an *Epimedium sagittatum* material which has been standardized to include 10% icariin can be included in the nutritional composition. Additionally or alternatively, in accordance with certain other embodiments, icariin or another botanical source of icariin can be included in the nutritional composition.

Kudzu (*Pueraria lobata*) is a Japanese creeper associated with the legume family. In accordance with certain embodiments, a kudzu material which has been standardized to include 10% robinin can be included in the nutritional composition. Robinin has antioxidant properties and is an anabolic flavonoid. Kudzu materials are also believed to promote increases in muscle mass.

Loquat leaf extract is believed to improve insulin sensitivity, increase protein turnover rate, and stimulate growth. In accordance with certain embodiments, a loquat leaf extract which has been standardized for 10% maslinic acid can be included in the nutritional composition. Olive leaf extract is believed to improve insulin sensitivity, increase protein turnover rate, and stimulate growth. In accordance with certain embodiments, an olive leaf extract which has been standardized for 10% maslinic acid can be included in the nutritional composition.

Hawthorn (*Crataegus monogyna*) is a hedge plant in the rose family. Active compounds found in hawthorn materials include hyperin (hyperoside), an antioxidant, and various anabolic flavonoids. Hawthorn is also known to be an anti-inflammatory agent and is suspected to help increase muscle mass. In accordance with certain embodiments, the nutritional supplement can include or contain a hawthorn material which has been standardized to include 10% hyperin (Hyperoside).

Shilajit moomiyo is an adaptogenic herb which can be used to enhance physical and mental performance. Shilajit is believed to amplify the benefits of other herbs by enhancing their bio-availability. Shilajit is also believed to increase protein synthesis, growth rate and/or energy intake. Suitably, the nutritional composition can include a Shilajit material or extract which has been standardized to include or contain 10% humic acid and/or 10% fulvic acid. In accordance with certain other embodiments, the nutritional composition can alternatively and/or additionally contain fulvic acid, humic acid, and/or another botanical, natural, or herbal source of fulvic acid and/or humic acid.

The nutritional composition can further include one or more free amino acids including essential amino acids and/or branched chain amino acids. Generally, it has been found that ingesting free amino acids has a beneficial impact on muscle performance and recovery and promotes anabolism. Essential amino acids have generally been shown to have both an anti-catabolic effect and an anabolic effect during exercise and in the post-exercise period while branched chain amino acids (BCAAs), particularly leucine, have been shown to preserve muscle and decrease protein breakdown during times of weight loss or other catabolic circumstances.

Branched chain amino acids consumed during and post workout are thought to spare muscle glycogen, promote anabolism and anti-catabolism, promote recovery, promote alanine and glutamine production, and regulate fatigue (lactic acid) and DOMS (Delayed Onset Muscle Soreness).

Free amino acids which can be utilized in the nutritional composition include, but are not limited to, essential amino acids selected from histidine, methionine, phenylalanine, lysine, threonine, and combinations thereof, and branched chain amino acids (BCAAs) selected from isoleucine, leucine, valine, and combinations thereof, and/or salts, analogues, esters, ethers, and derivatives thereof.

The essential amino acids histidine, methionine, threonine, lysine, phenylalanine, leucine, isoleucine, and valine are amino acids not made by the body and must be consumed from food or supplements. The nutritional composition and methods disclosed herein take full advantage of the ergogenic benefit of combining carbohydrates and essential amino acids.

Additional components or compounds which can be utilized in the nutritional composition include: carbohydrates such as, for example, inulin and/or fructooligosaccharides; effervescent delivery agents such as, for example, bicarbonate compounds; creatine transport aides and/or creatine precursors such as, for example, guanidinopropionic acid, glycocyamine, and/or trimethylglycine (betaine); anti-fatigue agents such as, for example, beta-alanine, PEAK ATP® adenosine 5' triphosphate (available from TSI Health Sciences, Inc. Missoula, Mont.), and/or creatinol-O-phosphate; electrolytes such as, for example, glycerol stearate and additional sources of calcium, magnesium, potassium, and/or sodium; and excipients such as, for example, calcium silicate, malic acid, and/or citric acid.

The nutritional compositions disclosed herein can be administrated orally as an effective means of regulating athletic function. In addition to peroral use, other routes such as transdermal, sublingual, intranasal, or parenteral, can be used to effectively administer the disclosed nutritional compositions. Other dosage forms and applications include capsules, tablets, caplets, liquids, beverages, liquid capsules, dissolvable films, powders, sprays or functional food products.

Solid nutritional compositions for oral administration in connection with a method for promoting anabolism during exercise may optionally contain, in addition to the above enumerated nutritional composition ingredients or compounds: carrier materials such as corn starch, gelatin, acacia, microcrystalline cellulose, kaolin, dicalcium phosphate, calcium carbonate, sodium chloride, alginic acid, and the like; disintegrators including, microcrystalline cellulose, alginic acid, and the like; binders including acacia, methylcellulose, sodium carboxymethylcellulose, polyvinylpyrrolidone, hydroxypropyl methylcellulose, ethyl cellulose, and the like; and lubricants such as magnesium stearates, stearic acid, silicone fluid, talc, waxes, oils, colloidal silica, and the like. The usefulness of such excipients is well known in the art.

Liquid nutritional compositions for oral administration in connection with a method for promoting anabolism during exercise can be prepared in water or other aqueous vehicles. In addition to the above enumerated ingredients or compounds, liquid nutritional compositions can include suspending agents such as, for example, methylcellulose, alginates, tragacanth, pectin, kelgin, carrageenan, acacia, polyvinylpyrrolidone, polyvinyl alcohol, and the like. The liquid nutritional compositions can be in the form of a solution, emulsion, syrup, gel, or elixir including or containing, together with the above enumerated ingredients or compounds, wetting agents, sweeteners, and coloring and flavoring agents. Various liquid and powder nutritional compositions can be prepared by conventional methods.

As disclosed herein, a method for promoting anabolism during exercise includes orally administering to an individual engaged in exercise or physical activity a nutritional composition comprising at least one PPAR agonist and at least one PGC-1alpha agonist. The nutritional composition can additionally optionally include or contain one or more of: a creatine containing component; an anabolic stimulant; a central nervous system stimulant; a nitric oxide stimulant; an energy source or energy producing agent; a compound that enhances or induces protein synthesis; an antioxidant; an agent to improve insulin sensitivity; and/or compounds that enhance the bioavailability of other ingredients.

Oral daily doses of the nutritional composition can be between about 1 to about 1000 grams, suitably between about 1 to about 100 grams, or, between about 1 to about 30 grams. One exemplary daily dosing schedule can include one serving on training days. In another embodiment, multiple servings can be administered in a day if an individual engages in multiple training sessions (i.e., one dose or serving can be administered during each training session).

The nutritional composition and methods described above may be further understood in connection with the following Example.

EXAMPLE 1

In accordance with one embodiment, a serving of a nutritional composition can optionally include or consist of the following ingredients:

TABLE 1

| Ingredient | Function |
| --- | --- |
| *Epimedium sagittatum* standardized for 10% icariin | PPAR and PGC-1alpha Agonists |
| Piceatannol | |
| *Epimedium grandiflorum* | |
| Sodium pyruvate | |
| Japanese Knotweed | |
| trans-resveratrol | |
| *Rhodiola rosea* extract (root) (3% Rosavins and 1% Salidrosides) | |
| Pterostilbene (resveratrol analog) | |
| Creatine (including salt or solvate) | Sources of creatine |
| Creatine heptyl ester | |
| Creatine ethyl ester | |
| Creatinol-O-Phosphate | |
| N-phosphatidyl creatine heptanoate ester | |
| Ethyl 2-[N-1-(hexadecanamido)aminomethyl)-N-methylamino]acetate | |
| (reduced Creatine Palmitoyl Ethyl Ester HCl) | |
| Heptanol | Anabolic and/or central nervous system stimulants |
| Heptaminol | |
| L-lyxoflavin | |
| *Oxytropis muricata* | |
| Hydroxyphenethylamine | |
| N-benzoyl-2-hydroxyphenethylamine | |
| N-nicotinoyl-2-hydroxyphenethylamine | |
| *Echeveria glauca* | Energy sources |
| Sodium pyruvate | |
| *Rhodiola rosea* | |
| *Panax gingseng* (Acceleris ®) | |
| Alpha-hydroxy-isovaleric acid | Protein synthesis/ increased growth rate |
| Alpha-hydroxy-isocaproic acid | |
| Alpha-hydroxy-beta-methyl valeric acid | |
| Alpha-Hydroxy-gamma-methylthiobutyric acid | |
| Alpha-Hydroxy-beta-phenylpropionic acid | |
| Alpha-Hydroxy-beta-imidazolepropionic acid | |
| Alpha-Hydroxy-beta-hydroxybutyric acid | |
| Alpha-Hydroxy-gamma-aminocaproic acid | |
| Alpha-Hydroxy-gamma-guanidinovaleric acid | |
| Shilajit moomiyo extract with 10% fulvic acid and 10% humic acid | |
| Loquat leaf extract standardized for 10% maslinic acid | |
| Lespedine (kamferol-3,7-dirhamnoside) | |

TABLE 1-continued

| Ingredient | Function |
| --- | --- |
| Kudzu (*Pueraria lobata*) standardized for 10% robinin | Antioxidant/ improves muscle mass |
| Hawthorn (*Crataegus monogyna*) standardized for 10% hyperin | |
| Lespedine (kamferol-3,7-dirhamnoside) | |
| Loquat leaf extract standardized for 10% maslinic acid | Improve insulin sensitivity |

Acceleris® brand ginseng product is available from Unigen USA, Lacey, Wash.

The nutritional composition as in the above Example is prepared by mixing the components, i.e. chemical and botanical ingredients, in aqueous, lipid, or glycerol solutions. In addition, dried or powder formulations and/or tablets may be prepared. For example, a powder formulation would be an orally deliverable form, which would include the ingredients listed in Table 1, and including a customized flavor system. For example, powder formulations for aqueous suspension are contemplated. Thus, appropriate nutraceutical carriers and excipients comprise liquid, solid, and powder formulations.

EXAMPLE 2

In accordance with an embodiment, it is expected that a human subject using the nutritional composition of Example 1 by oral administration will show an increase in anabolism after multiple days of use. One expected measure of increased anabolism will be enhanced or increased muscle growth or size. It is also expected that a subject utilizing the nutritional composition of Example 1 will demonstrate enhanced physical performance and/or recovery from fatigue when combined with an established exercise regimen such as repetitive set weight lifting or weight training. One expected measure of enhanced physical performance will be enhanced or increased muscle growth or size. It is expected that total work output will be increased in a subject administered the nutritional composition of Example 1 by oral administration after multiple days of use. Total work output, expressed in units of joules per set, is measured as in U.S. Pat. No. 6,100,287, herein incorporated by reference.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A nutritional composition comprising:
   an amount of *Epimedium sagittatum* and phytanic acid effective to increase PPAR-alpha activity;
   an amount of *Rhodiola rosea* effective to increase PGC-1alpha activity;

at least one creatine compound selected from the group consisting of creatine, creatine heptyl ester, creatine ethyl ester, creatinol-O-Phosphate, a salt thereof, and combinations thereof; and a nutraceutically acceptable carrier, wherein the nutritional composition stimulates anabolism in an individual.

2. The nutritional composition of claim 1, further comprising at least one additional PPAR-alpha agonist selected from one or more of the group consisting of *Epimedium grandiflorum*, sodium pyruvate, and combinations thereof.

3. The nutritional composition of claim 1, further comprising at least one additional PGC-1alpha agonist selected from the group consisting of *Epimedium grandiflorum*, sodium pyruvate, piceatannol, and Japanese Knotweed.

4. The nutritional composition of claim 3, wherein the at least one additional PPAR-alpha agonist and the at least one additional PGC-1alpha agonist are the same component.

5. The nutritional composition of claim 1, further including at least one of a component selected from the group consisting of heptanol, heptaminol, L-lyxoflavin, *Oxytropis muricata*, hydroxyphenethylamine, N-benzoyl-2-hydroxyphenethylamine, N-nicotinoyl-2-hydroxyphenethylamine, *Echeveria glauca, Panax gingseng*, alpha-hydroxyisovaleric acid, alpha-hydroxyisocaproic acid, alpha-hydroxy-beta-methyl valeric acid, alpha-hydroxy-gamma-methylthiobutyric acid, alpha-hydroxy-beta-phenylpropionic acid, alpha-hydroxy-beta-imidazolepropionic acid, alpha-hydroxy-beta-hydroxybutyric acid, alpha-hydroxy-gamma-aminocaproic acid, alpha-hydroxy-gamma-guanidinovaleric acid, kamferol-3,7-dirhamnoside, Shilajit moomiyo extract, Kudzu, Hawthorn, Loquat leaf extract, and mixtures thereof.

6. A method for increasing anabolism in a human subject during physical activity, the method comprising administering to the subject an effective amount of a nutritional composition according to claim 1.

7. The method of claim 6, wherein the effective amount of the nutritional composition is a daily dose from about 1 gram to about 100 grams.

8. The method of claim 6, wherein the nutritional composition further comprises at least one of a component selected from the group consisting of heptanol, heptaminol, L-lyxoflavin, *Oxytropis muricata*, hydroxyphenethylamine, N-benzoyl-2-hydroxyphenethylamine, N-nicotinoyl-2-hydroxyphenethylamine, *Echeveria glauca, Rhodiola rosea, Panax gingseng*, alpha-hydroxyisovaleric acid, alpha-hydroxyisocaproic acid, alpha-hydroxy-beta-methyl valeric acid, alpha-hydroxy-gamma-methylthiobutyric acid, alpha-hydroxy-beta-phenylpropionic acid, alpha-hydroxy-beta-imidazolepropionic acid, alpha-hydroxy-beta-hydroxybutyric acid, alpha-hydroxy-gamma-aminocaproic acid, alpha-hydroxy-gamma-guanidinovaleric acid, kamferol-3,7-dirhamnoside, Shilajit moomiyo extract, Kudzu, Hawthorn, Loquat leaf extract, and mixtures thereof.

9. The method of claim 6, wherein said method increases total work output.

10. The method of claim 6, wherein said method increases muscle growth.

* * * * *